United States Patent
Holmström et al.

(10) Patent No.: US 8,308,649 B2
(45) Date of Patent: Nov. 13, 2012

(54) IMPLANTABLE CARDIAC DEVICE AND METHOD FOR MONITORING THE STATUS OF A CARDIOVASCULAR DISEASE

(75) Inventors: Nils Holmström, Järfälla (SE); Malin Öhlander, Stockholm (SE); Kjell Norén, Solna (SE); Andreas Blomqvist, Spånga (SE); Karin Ljungström, Hässelby (SE)

(73) Assignee: St. Jude Medical AB, Veddestavagen, Jarfalla (SE)

( * ) Notice: Subject to any disclaimer, the term of this patent is extended or adjusted under 35 U.S.C. 154(b) by 640 days.

(21) Appl. No.: 12/528,653

(22) PCT Filed: Mar. 23, 2007

(86) PCT No.: PCT/SE2007/000288
§ 371 (c)(1), (2), (4) Date: Aug. 26, 2009

(87) PCT Pub. No.: WO2008/118041
PCT Pub. Date: Oct. 2, 2008

(65) Prior Publication Data
US 2010/0121400 A1      May 13, 2010

(51) Int. Cl.
*A61B 5/02* (2006.01)
(52) U.S. Cl. ......................... 600/508; 600/547
(58) Field of Classification Search .................. 600/508, 600/547
See application file for complete search history.

(56) References Cited

U.S. PATENT DOCUMENTS

| | | |
|---|---|---|
| 5,645,570 A | 7/1997 | Corbucci |
| 6,527,729 B1 | 3/2003 | Turcott |
| 6,600,949 B1 | 7/2003 | Turcott |
| 7,177,686 B1 | 2/2007 | Turcott |
| 7,206,636 B1 | 4/2007 | Turcott |
| 2003/0163034 A1 | 8/2003 | Dekker |
| 2004/0260186 A1 | 12/2004 | Dekker |

OTHER PUBLICATIONS

"Altered Blood Pressure Variability in Patients With Congestive Heart Failure," Radaelli et al., J/Hypertens., vol. 71, No. 12 Part 2, (1999) pp. 1905-1910.
"Absence of Low-Frequency Variability of Sympathetic Nerve Activity in Severe Heart Failure," van de Borne et al., Circulation, vol. 95 (1997) pp. 1449 1545.
Heart Rate Variability as an Assessment of Cardiovascular Status, Fleisher, J. of Cardiothoracic and vascular Anesthesia, vol. 10, No. 5 (1996) pp. 659-671.
The Enignma of Mayer Waves: Facts and Models,: Julien, Cardiovascular Research, vol. 70 (2006) pp. 12-21.

*Primary Examiner* — Carl H Layno
*Assistant Examiner* — Yun Haeng Lee

(57) ABSTRACT

An implantable cardiac device has a heart stimulator for electrically stimulating the heart of a patient, detector that measures a physiologic parameter that is affected by the status of a cardiovascular disease associated with sympathetic activation, a signal processor that determines at least one of a low frequency, LF, and a very low frequency, VLF, Mayer wave component in the measured parameter, and analyzer that automatically analyzes the determined Mayer wave component in relation to a predetermined reference value to determine the status of the cardiovascular disease. The detector is a cardio-mechanical parameter detector that measures, as said physiologic parameter, a mechanical change in at least one of the four chambers of the heart. In a corresponding method for monitoring the status of a cardiovascular disease associated with sympathetic activation of a patient having an implantable electric heart stimulator a physiologic parameter affected by the cardiac disease is measured. At least one of a low frequency, LF, and a very low frequency, VLF, Mayer wave component in the parameter is determined, and the wave component is analyzed in relation to a predetermined reference value to determine the status of the cardiovascular disease. A mechanical change in at least one of the four chambers of the heart is measured as the physiologic parameter.

40 Claims, 4 Drawing Sheets

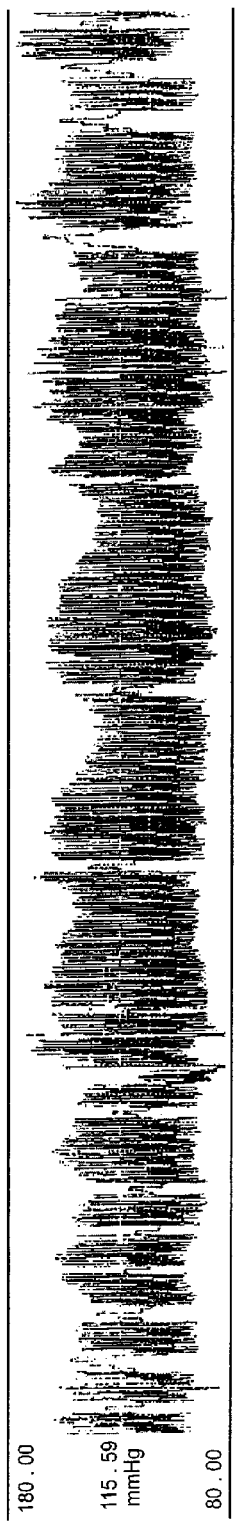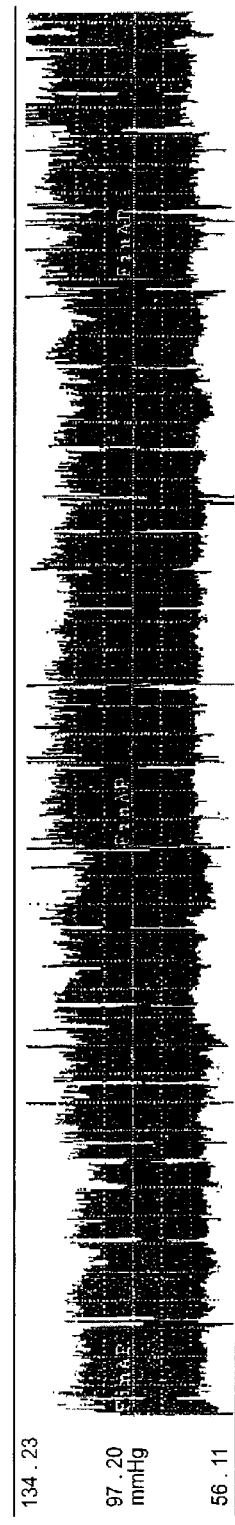

IMPLANTABLE CARDIAC DEVICE AND METHOD FOR MONITORING THE STATUS OF A CARDIOVASCULAR DISEASE

BACKGROUND OF THE INVENTION

1. Field of the Invention

The present invention relates to an implantable cardiac device of the type having a heart stimulator for electrically stimulating the heart of a patient, detecting means for measuring a physiologic parameter that is affected by the status of a cardiovascular disease associated with sympathetic activation, signal processing means for determining at least one of a low frequency, LF, and a very low frequency, VLF, Mayer wave component in the measured parameter, and an analyzer for analyzing the determined Mayer wave component in relation to a predetermined reference value to determine the status of the cardiovascular disease, and to a corresponding method for monitoring the status of a cardiovascular disease associated with sympathetic activation of a patient having an implantable electric heart stimulator.

2. Description of the Prior Art

Heart Rate Variability, HRV, has been suggested as a parameter reflecting the activity in the Autonomic Nervous System, ANS. This activity is altered with the health of a patient. The pathophysiologic activation of ANS at heart failure and other diseases reveal the level of stress and unbalance in the body. HRV diminishes during heart disease and can for instance be used to detect and show deterioration of a Heart Failure, HF, and predict sudden cardiac death. Unfortunately HRV can only be measured during sinus rhythm. For patients having their heart rate modulated to a large extent by an Implantable Cardiac Device, such as a pulse generator or ICD, calculation of HRV is not feasible.

Mayer waves are low frequency oscillations in ANS causing a. o. blood pressure variations and HRV. The phenomenon is not well understood but its existence and response to heart disease, and also other circumstances, have been confirmed, see e.g. Cardiovascular Research, 70, 2006, pp. 12-21, Circulation 95, 1997, pp. 1449-54, and J. Hypertens., 17(12 Pt 2), December 1999, pp. 1905-10.

EP 1 151 719 discloses an implantable apparatus for monitoring the condition of a heart failure patient using respiration patterns. The patient's respiratory patterns are monitored to identify periodic breathing or Cheyne-Stokes respiration. Different parameters are suggested for assessing Cheyne-Stokes respiration, like mechanical changes of thorax due to breathing, changes in blood and tissue pH, $CO_2$ concentration and the R-R interval, extracted from ECGs. From R-R interval information measures of HRV are derived and the presence of respiratory fluctuations as well as Mayer waves are tested by examining the variability over specific frequency ranges. The absence of fluctuations in the respiratory fluctuation frequency band as well as in the Mayer waves frequency bands is interpreted as a worsening of the disease status.

In U.S. Pat. No. 5,645,570 an implantable device for detecting the sympatho-vagal balance of a patient is described. From ECGs the variability of the heart rate is evaluated as the number of consecutive R-R intervals, which differ from one another by at least a minimum threshold. If this number satisfies a predetermined intervention criterion a therapeutic device for the patient is triggered.

In Lee A. Fleisher, "Heart Rate Variability as an Assessment of Cardiovascular Status", Journal of Cardiothoracic and Vascular Anesthesia, Vol. 10, No. 5 (August), 1996, pp. 659-671 the usage is described of time intervals between consecutive heart beats, preferably the R-R intervals, for evaluating HRV. The R-R intervals are derived from ECGs. The evaluation can be made in the time domain or in the frequency domain. In the latter case the power spectrum in the Mayer wave frequency range can be used to predict mortality of Congestive Heart Failure, CHF, patients.

The above discussed prior art for HRV analysis, e.g. the use of the R-R interval measurements for assessment of HRV, is applicable only to patients in sinus rhythm, cf. e.g. the above mentioned article Lee A. Fleisher, "Heart Rate Variability as an Assessment of Cardiovascular Status", Journal of Cardiothoracic and Vascular Anesthesia, Vol. 10, No. 5 (August), 1996, p. 662, left column, third paragraph. For patients having their heart rate modulated or controlled by a heart stimulator it is, however, not possible to use the traditional HRV analysis.

It has, however, appeared that e.g. variability of blood pressure and blood flow are possible markers for studying pathophysiologic activation of ANS at heart failure and other diseases. The strength of the arterial blood pressure oscillations, for instance, is highly affected at some cardiovascular diseases associated with sympathetic activation, e.g. congestive heart failure, CHF. There are also physiologic parameters other than the blood pressure that are affected during sympathetic activation. Thus the left ventricular tension and the left ventricular contraction pattern are also indicators of sympathetic activation as well as the mechanical AR-interval and pre-ejection time.

SUMMARY OF THE INVENTION

An object of the present invention is to provide a device and propose a method for monitoring the status of a cardiovascular disease associated with sympathetic activation which can be used also for patients having their heart rate modulated by a heart stimulator.

The above object is achieved by an implantable device of the type initially described wherein, according to the invention a cardio-mechanical parameter detector is provided that measures mechanical change in at least one of the four chambers of the heart. The corresponding signal is processed for determining at least one of the low frequency, LF, and the very low frequency, VLF, Mayer wave components in the measured parameter. This Mayer wave component is then analysed for determining the status of the cardiovascular disease of the patient. In this way it is possible to monitor the status of a cardiovascular disease of a patient having a heart stimulator, and not only monitor the present status of a disease but also to predict incipient heart events. An early detection of a change in the patient's status is thus possible, and a flag can then be set indicating that the patient should visit his doctor for a health control and possible change in drug administration. Normally it is wanted to foresee Acute Decompensated Heart Failure, ADHF, in an early state. 80% of these cases involve patients having previously diagnosed or chronic heart failure. Each episode of ADHF carries a higher mortality. Being able to prevent episodes of ADHF before they occur by studying Mayer waves would therefore benefit the prognosis and save lives.

In advantageous embodiments of the device according to the invention the cardio-mechanical parameter detector measures the electric transcardiac bio-impedance. The cardio-mechanical parameter detector preferably measures the electric bio-impedance quadropolarly between right atrium and right ventricle, or bipolarly in the right ventricle. Signals measured in this way are more stable and predictable and seems to mirror the left ventricular contractions as well. The electric bio-impedance, however, also can be measured over the left ventricle, LV. The cardio-mechanical parameter detector then can include two electrodes, one adapted for positioning in the right ventricle and the other adapted for positioning in a coronary vein on the left ventricle. The impedance measured between these electrodes mirrors the left ventricular volume. Other positionings of the electrodes are also possible. The electrodes can e.g. be adapted for epicardial location. As mentioned above the pathophysiologic activation of ANS at heart failure reveals the level of stress and unbalance in the body, and the variety of blood pressure and blood flow are possible markers that can be studied for this purpose. The left ventricular contraction pattern can be monitored by the above mentioned measurements of the electric bio-impedance over LV. Oscillations in LV pressure are indicated by stroke volume variations measured by the electric bio-impedance over LV.

Respiration modulation of the ANS signal can be a problem. The respiration frequency is, however, normally higher than the physiologic oscillations generated by ANS, viz. Mayer waves. Since the Mayer waves are low, 3-140 mHz, compared to the respiration component, ~200 mHz, the respiration component can be eliminated by appropriate filtering of the peak to peak amplitude, the time integrated area of the measured impedance signal, or the contraction strength obtained from the measured dynamic impedance signal. Both respiration and heart rhythm can be measured separately, e.g. by bio-impedance measurements or electric signal detection, which also facilitates discrimination of respiration components from Mayer waves components.

In other advantageous embodiments of the device according to the invention the cardio-mechanical parameter detector includes a pressure sensor for measuring blood pressure variations in one of the four chambers of the heart. The pressure sensor can then be a piezoelectric sensor or a membrane sensor.

The myocardial contractility is also affected during sympathetic activation. The left ventricular contraction pattern can be monitored by measurements of the bio-impedance over LV, as discussed above. The left ventricular muscular tension is an indicator of sympathetic activation which can be monitored by a sensor too. According to still other advantageous embodiments of the invention the left ventricular contractility is therefore measured. The slope of a predetermined portion of the signal, corresponding to the measured bio-impedance, is determined as a measure of the left ventricular contractility according to an advantageous embodiment of the method according to the invention. The cardio-mechanical parameter detector of the device according to the invention can include a sound sensor for picking up heart sound amplitudes indicating mitral and/or aortic valve closures as measures of ventricular contractility. The cardio-mechanical parameter detector can also include a tension sensor adapted for positioning on the epicardium, or in the epicardial space.

In another advantageous embodiment of the device according to the invention the cardio-mechanical parameter detector measures mechanical changes in at least one of the quantities the mechanical atrioventricular conduction time, i. e. the mechanical AR-interval, and pre-ejection period as the physiologic parameter affected by the status of a cardiovascular disease associated with sympathetic activation and thus useful for studying sympathetic activation.

In other advantageous embodiments of the device according to the invention the cardio-mechanical parameter detector measures the physiologic parameter for a period of at least several minutes, and the signal processor calculates at least one corresponding data sample per heartbeat. A memory is provided for storing the data samples and a filter is provided for filtering the stored data and determining the amplitudes of LF and/or VLF Mayer wave components. A Fourier transforming unit can alternatively be provided for determining LF and/or VLF Mayer wave components of the measured physiologic parameter as well as the amplitudes of these components. Data are preferably measured continuously, with a frequency of e.g. 128 Hz, and at least one parameter data sample is calculated for every heartbeat as mentioned above. To be able to find the very low frequency Mayer oscillations, typically of 40 mHz, the recording of data must be performed during at least several minutes, such that a data string of at least a few hundred data are obtained for storage and further analysis.

In another advantageous embodiment of the device according to the invention the signal processor determines the spectrogram of at least one of the Mayer wave components, and the analyzer is adapted to analyze the determined spectrogram in relation to a predetermined template spectrogram to determine the status of the cardiovascular disease. Continuous recording of such a Mayer wave spectrogram can be used for early detection of a changed cardiac status of the patient.

In another advantageous embodiment of the device according to the invention an alerting unit is provided to alert the patient to contact a medical doctor, if the deviation of the determined Mayer wave component from the reference value exceeds a predetermined threshold. If the Mayer wave oscillations decrease compared to the reference value or a normal template the risk of a coming cardiac event is increasing.

In another advantageous embodiment of the device according to the invention, the heart stimulator thereof includes a controller for controlling the heart stimulation therapy depending on detected status of the patient's heart disease. A timing of the electric stimulation or pacing therapy which is not optimized will create an increased sympathetic tonus. This will stress the autonomic regulation and reduce the variability of physiologic signals and Mayer wave oscillations. With an optimal pacing therapy, viz. optimal stimulation rate, and optimal AV- and VV-delays, the oscillation amplitude will be at its maximum.

BRIEF DESCRIPTION OF THE DRAWINGS

FIGS. 1 and 2 show dynamic blood pressures measured non-invasively for two different patients, respectively.

DESCRIPTION OF THE PREFERRED EMBODIMENTS

FIGS. 1 and 2 show dynamic blood pressures measured non-invasively on two different patients as a function of time.

FIG. 1 shows pressure variations measured on a female, Congestive Heart Failure, CHF, patient of 64 years, NYHA class 2, i.e. class 2 according to the New York Heart Association classification, and suffering from Left Bundle Branch Block, LBBB. The time scale of the shown diagram is 8 sec/division. As appears the systolic pressure varies with a Mayer wave frequency of 20-30 mHz and the average systolic pressure amounts to 115.59 mmHg.

FIG. 2 shows corresponding pressure variations measured on a male CHF patient of 69 years, NYHA class III and suffering from LBBB. The time scale of the shown diagram is 20 sec/division. The systolic pressure varies with a Mayer wave frequency of 15-20 mHz and the average systolic pressure amounts to 97.20 mmHg.

A periodic Mayer wave variability appears clearly in the measured blood pressures of both these CHF patients.

Figure 3:
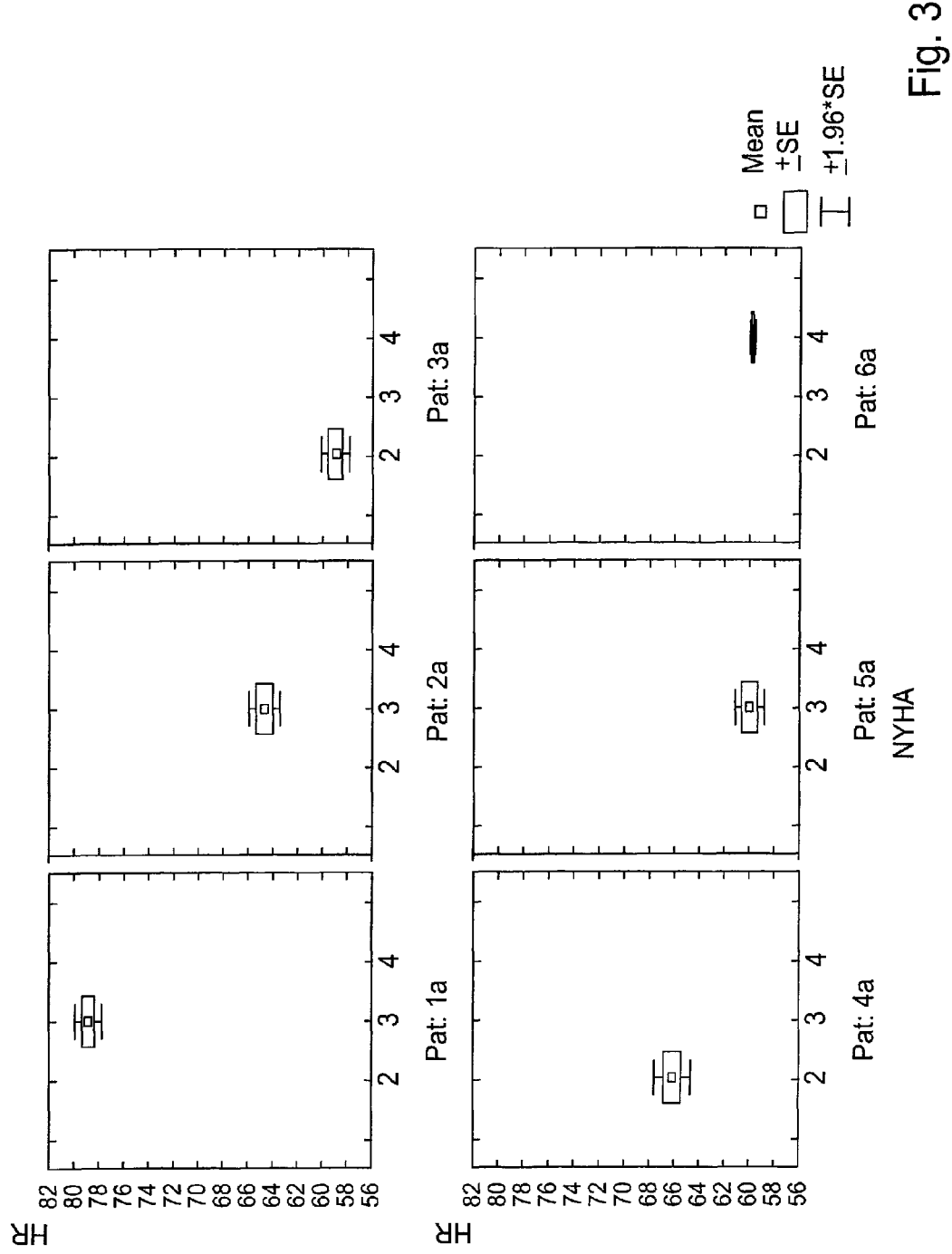
FIG. 3 shows heart rates HR measured for patients in various NYHA (New York Heart Association) classes.

FIG. 3 illustrates results of heart rates, HR, measurements on two NYHA class 2 patients, three NYHA class 3 patients and one NYHA class 4 patients. For each patient mean value, standard error, SE, and ±1.96*SE are indicated for the measured HR. The diagrams in FIG. 3 show that SE decreases with increasing NYHA class number, viz. HRV decreases with increasing NYHA class or with increasing severity of the cardiac disease.

Figure 4:
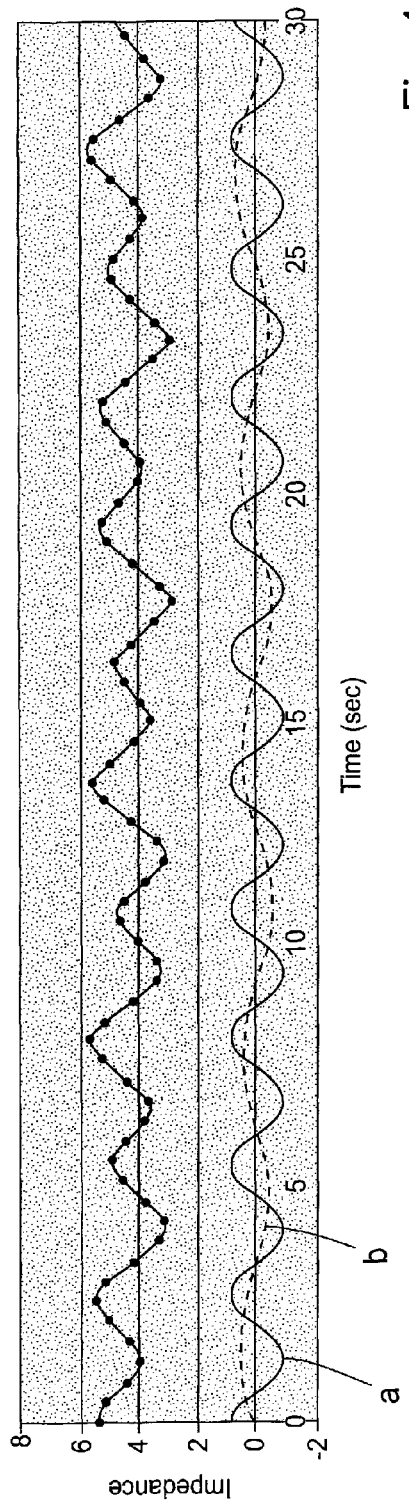
FIG. 4 shows a physiologic parameter calculated from a measured impedance signal together with respiration and Mayer wave oscillations.

The upper curve in FIG. 4 shows qualitatively a physiologic parameter as a function of time, calculated from an impedance signal measured over LV. Each dot of the curve represents a calculated parameter value for each heartbeat.

The parameter values could be calculated from another measured physiologic signal as well.

The lower curve a in FIG. 4 represents a Mayer wave and the lower curve b the respiration. Both the Mayer wave and the respiration are influencing the measured parameter depending on the physiologic state of the patient.

The measurements illustrated in FIG. 4 are performed continuously. The measurements could, however, alternatively be performed periodically, e. g. once per hour.

Figure 5:
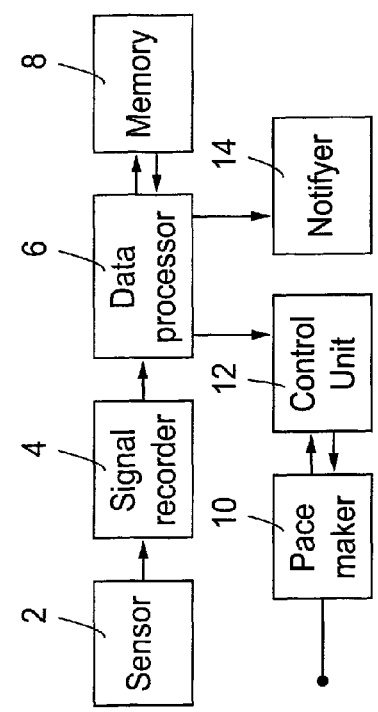
FIG. 5 is a block diagram illustrating an embodiment of the device according to the invention/

FIG. 5 is a block diagram of an embodiment of the device according to the invention. The device has a sensor 2 for measuring a physiologic parameter that is affected by the status of a cardiovascular disease associated with sympathetic activation. A signal recorder 4 is provided for recording the parameter data. Data are measured continuously, e.g. with a frequency of 128 Hz, and at least one parameter data value is calculated for each heartbeat. To be able to find VLF Mayer oscillations, of typically 40 mHz, the recording must be performed during several minutes. The data are processed in a data processor 6 and a string of a few hundred data points are stored in a memory 8. In the signal processor 8 the data string is digitally filtered to separate the Mayer wave components and the respiration component and to determine their amplitudes. The spectrogram thus determined is also stored in the memory 8.

As an alternative the data processor 6 can include a Fourier transforming unit that localizes the mentioned frequency components and determines their amplitudes.

The data processor 6 also includes an analyzer for analyzing the determined Mayer wave components in relation to a predetermined reference value to determine the status of the cardiovascular disease. In practice the analyzer is preferably adapted to analyze the determined Mayer wave spectrogram in relation to a predetermined template spectrogram to determine the status of the cardiovascular disease.

The embodiment in FIG. 5 also has a heart stimulator in the form of a pacemaker 10 for delivering electric stimulation pulses to a patient's heart. A control unit 12 is provided to receive from the data processor 6 the result of the above described analysis for controlling the pacemaker therapy depending on the detected status of the patient's cardiovascular disease.

A continuous recording of the Mayer wave spectrogram can be used for making an early detection of a changed cardiac status, as discussed above. The device shown in FIG. 5 thus also has a notifyer 14 connected to the data processor 6 for setting a flag indicating that the patient should visit his medical doctor for a health control or change in drug administration, if the analysis shows that the determined Mayer wave component deviates from a predetermined reference value with more than a predetermined threshold.

Figure 7:
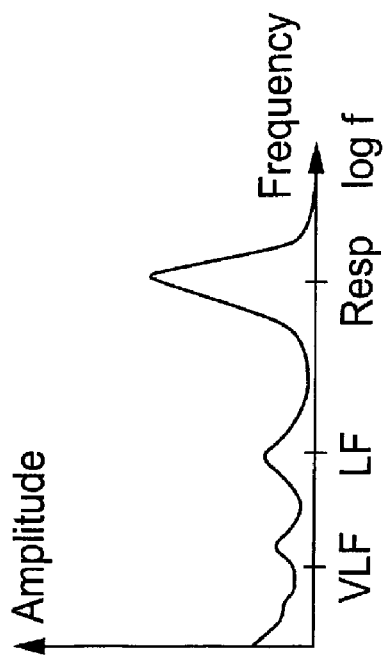
FIGS. 6 and 7 qualitatively show frequency spectra of a measured physiological parameter having VLF and LF Mayer wave components, as well as a respiration frequency component, for two patients with different health status, respectively/
Figure 6:
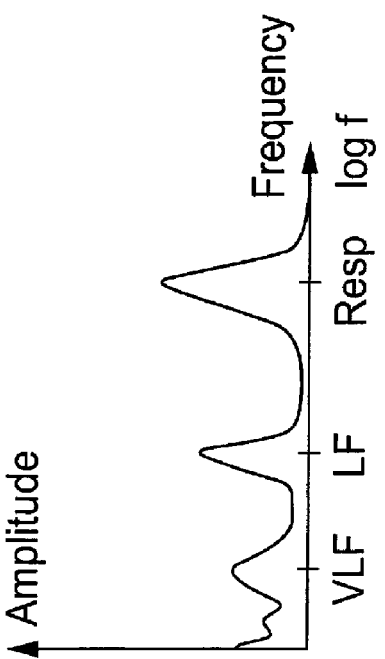

As disclosed above a physiologic parameter which is affected by the status of a cardiovascular disease associated with sympathetic activation is measured e.g. by the electric bio-impedance. Appropriate filtering of the peak to peak amplitude, or the integrated area of the systolic contraction strength in the dynamic impedance signal is made. By this filtering the Mayer waves can be discriminated from the respiration rhythm, because the Mayer wave oscillations have a significantly lower frequency the respiration signal. This is illustrated in FIGS. 6 and 7 and also by curves a and b in FIG. 4. Both respiration and the heart rhythm can be measured separately, which facilitates distinguishing the two types of waves.

FIGS. 6 and 7 thus qualitatively illustrate frequency spectra of a physiologic parameter, e.g. the systolic blood pressure, with strong VLF and LF Mayer waves present in FIG. 6 and with weak Mayer waves present in FIG. 7. The amplitude of the respiration component, Resp, is substantially constant in the two Figures.

The strong Mayer wave oscillations in FIG. 6 may be a good sign for the status of the patient's health. In the situation illustrated in FIG. 7, on the other hand, the amplitude of the Mayer wave oscillations has decreased compared to a normal template, which means an increased risk for a preceding heart event.

Also, if the timing of the pacing therapy is not optimized an increased sympathetic tonus will be created. This will stress the autonomic regulation and reduce the variability of physiological signals, and consequently reduce the Mayer wave oscillations, as illustrated in FIG. 7. An optimal pacing therapy will, however, result in a large signal variety and a maximum Mayer wave oscillation amplitude, cf. FIG. 6.

The LF and VLF Mayer wave oscillations should be measured with the patient at rest, when few other disturbances are present The blood pressure and the left ventricular volume will vary with the body position and workload, which makes detection of Mayer waves difficult for unstable situations of the patient. It is also important that the patient is awake, i.e. conscious, at the measurement. Activity sensors and body position sensors as well as a real time clock can therefore be used to ensure repetitive and correct measuring conditions.

As mentioned above a reference value or a reference template of normal HRV is used in the analysis of the measured Mayer wave oscillations. Such a reference value or template is preferably created automatically during the first day(s) and stored in the device. This procedure for determining the reference value or template is repeated after a follow-up, when the patient's health status is known.

The low frequency wave oscillations in the ANS, which cause detectable variations in several different physiologic parameters and which are called Mayer waves herein, are also named in the literature as Traube-Hering-Mayer waves, Hering's waves, Traube's waves, Traube-Hering curves, Traube-Hering waves and Mayer's waves.

Although modifications and changes may be suggested by those skilled in the art, it is the intention of the inventors to embody within the patent warranted heron all changes and modifications as reasonably and properly come within the scope of their contribution to the art.

We claim as our invention:

1. An implantable cardiac device comprising:

a cardio-mechanical parameter detector configured for in vivo placement in a living subject, that detects a physiologic parameter representing a mechanical change in at least one chamber of the heart of the subject that is affected by status of cardiovascular disease in the subject associated with sympathetic nerve activation, and that emits a detector output corresponding to said physiologic parameter;

a housing configured for in vivo implantation in the subject;

a processor in said housing and in communication with said cardio-mechanical detector to receive said detector output therefrom, that extracts a Mayer wave component, selected from the group consisting of a low frequency Mayer wave component and a very low frequency Mayer wave component, from said detector output; and an analyzer in said housing that compares the extracted Mayer wave component to a predetermined reference to obtain an analysis result indicative of said status of cardiovascular disease, said analyzer emitting an analyzer output signal corresponding to said analysis result.

2. A device as claimed in claim 1 wherein said cardio-mechanical parameter detector measures electric transcardiac bioimpedance of the heart of the subject.

3. A device as claimed in claim 1 wherein said cardio-mechanical parameter detector measures electric bio-impedance quadropolarly between the right atrium and the right ventricle of the heart of the subject.

4. A device as claimed in claim 1 wherein said cardio-mechanical parameter detector measures electric bio-impedance bipolarly in the right ventricle of the heart of the subject.

5. A device as claimed in claim 1 wherein said cardio-mechanical parameter detector measures electric bio-impedance over the left ventricle of the heart of the subject.

6. A device as claimed in claim 5 wherein cardio-mechanical parameter detector comprises two electrodes, a first of said electrodes being configured for positioning in the right ventricle of the heart of the subject and a second of the electrodes being configured for positioning in a coronary vein on the left ventricle of the heart of the subject.

7. A device as claimed in claim 1 wherein said cardio-mechanical parameter detector measures an electric bio-impedance associated with the heart of the subject and comprises electrodes configured for epicardial location on the heart of the subject to measure said electric bio-impedance.

8. A device as claimed in claim 1 wherein said cardio-mechanical parameter detector comprises a pressure sensor that measures blood pressure variations in a chamber of the heart of the subject.

9. A device as claimed in claim 8 wherein said pressure sensor is selected from the group consisting of piezoelectric sensors and membrane sensors.

10. A device as claimed in claim 1 wherein said cardio-mechanical parameter detector is configured to measure left ventricular contractility in the heart of the subject.

11. A device as claimed in claim 10 wherein said cardio-mechanical parameter detector comprises a sound sensor that acoustically detects sound amplitudes indicating mitro valve closures or aortic valve closures, as a measure of said ventricular contractility.

12. A device as claimed in claim 10 wherein said cardio-mechanical parameter detector measures electric bio-impedance over the left ventricle, and emits a measured bio-impedance signal corresponding thereto, and wherein said analyzer is configured to automatically determine a slope of a predetermined portion of said measured bio-impedance signal as a measure of said left ventricular contractility.

13. A device as claimed in claim 1 wherein said cardio-mechanical parameter detector comprises a tension sensor configured for positioning at a location relative to the heart of the subject, selected from the group consisting of the epicardium and the epicardial space.

14. A device as claimed in claim 1 wherein said cardio-mechanical parameter detector measures mechanical changes in at least one quantity selected from the group consisting of mechanical AR-interval of the heart of the subject, and pre-ejection period of the heart of the subject.

15. A device as claimed in claim 1 wherein said cardio-mechanical parameter detector measures said physiologic parameter during a period of time comprising a plurality of minutes, and wherein said analyzer obtains at least one data sample of said physiologic parameter per heart beat of the subject.

16. A device as claimed in claim 15 comprising a memory in said housing in communication with said analyzer, in which data samples are stored respectively for a plurality of heartbeats, as stored data, and wherein said analyzer comprises a filter that filters said stored data to determine an amplitude of said Mayer wave component, for comparison to said reference to obtain said analysis result.

17. A device as claimed in claim 1 wherein said cardio-mechanical parameter detector measures mechanical changes in at least one of a mechanical AR-interval and pre-ejection period of the heart of the subject, and wherein said analyzer obtains at least one sample of said physiologic parameter per heart beat of the subject, and comprising a memory in said housing in communication with said analyzer in which a plurality of data samples are stored respectively for a plurality of heart beats, as stored data, and wherein said analyzer comprises a Fourier transforming unit that extracts said Mayer wave component, as well as an amplitude thereof, from said stored data for comparison to said reference to obtain said analysis result.

18. A device as claimed in claim 1 wherein said analyzer determines a spectrogram of said Mayer wave component, and compares said spectrogram to a predetermined template spectrogram, as said predetermined reference, to obtain said analysis result.

19. A device as claimed in claim 1 wherein said analyzer compares said Mayer wave component to said predetermined reference to obtain said analysis result, and comprising an alerting unit in said housing that emits a humanly perceptible alerting signal to the subject if a deviation of said Mayer wave component from said predetermined reference exceeds a predetermined threshold.

20. A device as claimed in claim 1 comprising a cardiac stimulator at least partially in said housing and configured to interact with the subject to stimulate the heart of the subject with stimulation therapy, and comprising a controller that controls said heart stimulator to modify said stimulation therapy dependent on said analysis result.

21. A method for monitoring status of cardiovascular disease, comprising the steps of:

making an in vivo detection of a physiologic parameter in a subject representing a mechanical change in at least one chamber of the heart of the subject that is affected by status of cardiovascular disease in the subject associated with sympathetic nerve activation, and generating an electrical signal corresponding to said physiologic parameter; supplying said signal to a processor and, in said processor extracting a Mayer wave component, selected from the group consisting of a low frequency Mayer wave component and a very low frequency Mayer wave component; and automatically comparing the extracted Mayer wave component to a predetermined reference to obtain an analysis result indicative of said status of cardiovascular disease, and generating an analysis signal corresponding to said analysis result.

22. A method as claimed in claim 21 comprising measuring electric transcardiac bioimpedance of the heart of the subject as said physiologic parameter.

23. A method as claimed in claim 21 comprising measuring electric bio-impedance quadropolarly between the right atrium and the right ventricle of the heart of the subject as said physiologic parameter.

24. A method as claimed in claim 21 comprising measuring electric bio-impedance bipolarly in the right ventricle of the heart of the subject as said physiologic parameter.

25. A method as claimed in claim 21 comprising measuring electric bio-impedance over the left ventricle of the heart of the subject as said physiologic parameter.

26. A method as claimed in claim 25 comprising detecting said physiologic parameter with a first electrode positioned in the right ventricle of the heart of the subject and a second electrode positioned in a coronary vein on the left ventricle of the heart of the subject.

27. A method as claimed in claim 21 comprising measuring an electric bio-impedance associated with the heart of the subject as said physiologic parameter using electrodes placed at an epicardial location on the heart of the subject.

28. A method as claimed in claim 21 comprising measuring blood pressure variations in a chamber of the heart of the subject as said physiologic parameter.

29. A method as claimed in claim 28 comprising measuring said blood pressure using a pressure sensor selected from the group consisting of piezoelectric sensors and membrane sensors.

30. A method as claimed in claim 21 comprising measuring left ventricular contractility in the heart of the subject as said physiologic parameter.

31. A method as claimed in claim 30 comprising measuring said ventricular contractibility using a sound sensor that acoustically detects sound amplitudes indicating mitro valve closures or aortic valve closures.

32. A method as claimed in claim 30 comprising measuring electric bio-impedance over the left ventricle, and generating a measured bio-impedance signal corresponding thereto, and automatically determining a slope of a predetermined portion of said measured bio-impedance signal as a measure of said left ventricular contractility.

33. A method as claimed in claim 21 comprising measuring tension as said physiologic parameter using a tension sensor configured for positioned at a location relative to the heart of the subject, selected from the group consisting of the epicardium and the epicardial space.

34. A method as claimed in claim 21 comprising measuring mechanical changes in at least one quantity selected from the group consisting of mechanical AR-interval of the heart of the subject, and pre-ejection period of the heart of the subject, as said physiologic parameter.

35. A method as claimed in claim 21 comprising measuring said physiologic parameter during a period of time comprising a plurality of minutes, and obtaining at least one data sample of said physiologic parameter per heart beat of the subject.

36. A method as claimed in claim 35 comprising electronically storing data samples respectively for a plurality of heartbeats, as stored data, and filtering said stored data to determine an amplitude of said Mayer wave component, for comparison to said reference to obtain said analysis result.

37. A method as claimed in claim 21 comprising measuring mechanical changes in at least one of a mechanical AR-interval and pre-ejection period of the heart of the subject as said physiologic parameter, and obtaining at least one sample of said physiologic parameter per heart beat of the subject, and electronically storing a plurality of data samples respectively for a plurality of heart beats, as stored data, and Fourier transforming the stored data to extract said Mayer wave component, as well as an amplitude thereof, for comparison to said reference to obtain said analysis result.

38. A method as claimed in claim 21 comprising determining a spectrogram of said Mayer wave component, and comparing said spectrogram to a predetermined template spectrogram, as said predetermined reference, to obtain said analysis result.

39. A method as claimed in claim 21 comprising comparing said Mayer wave component to said predetermined reference to obtain said analysis result, and emitting a humanly perceptible alerting signal to the subject if a deviation of said Mayer wave component from said predetermined reference exceeds a predetermined threshold.

40. A method as claimed in claim 21 comprising stimulating the heart of the subject with stimulation therapy, modifying said stimulation therapy dependent on said analysis result.

* * * * *